United States Patent [19]

Piteau et al.

[11] Patent Number: 4,612,143
[45] Date of Patent: Sep. 16, 1986

[54] PROCESS FOR THE PREPARATION OF FLUOROFORMATES

[75] Inventors: Marc Piteau, Itteville; Jean-Pierre Senet, La Chapelle la Reine; Patrick Wolf, Vert le Petit, all of France; Roy A. Olofson; Vu A. Dang, both of State College, Pa.

[73] Assignee: Societe Nationale des Poudres et Explosifs, Paris, France

[21] Appl. No.: 651,661

[22] Filed: Sep. 17, 1984

[51] Int. Cl.$^4$ .............................................. C07C 68/06
[52] U.S. Cl. .................................... 558/282; 558/280
[58] Field of Search ........................................ 260/463

[56] References Cited

U.S. PATENT DOCUMENTS 3,287,388  11/1966  Christe et al. ..................... 260/463
3,696,150  10/1972  Lichstein et al. .................. 260/463

FOREIGN PATENT DOCUMENTS 2816873  11/1978  Fed. Rep. of Germany.

OTHER PUBLICATIONS

Mitsubishi Chem., *Chemical Abstracts*, vol. 96:34601u.

Primary Examiner—Donald G. Daus
Assistant Examiner—Stephen M. Kapner
Attorney, Agent, or Firm—Bucknam and Archer

[57] ABSTRACT

A process for the preparation of fluoroformates of formula:

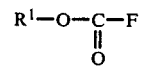

in which $R^1$ is a substituted or unsubstituted, saturated or unsaturated aliphatic, cycloaliphatic or polycyclic radical, or substituted or unsubstituted araliphatic radical or an aromatic radical, which consists of reacting a carbonate of formula:

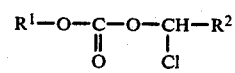

in which $R^1$ has the same meaning as hereinabove and $R^2$ is hydrogen, alkyl of 1–12 carbon atoms, cycloalkyl of 5–12 carbon atoms, saturated or unsaturated, unsubstituted or substituted by one or more halogen atoms or $R^2$ is aryl, unsubstituted or substituted by one or more halogen atoms, with an alkali or alkaline earth fluoride, ammonium fluoride or a quaternary ammonium fluoride, of formula $FNR^3R^4R^5R^6$, wherein $R^3$, $R^4$, $R^5$, $R^6$ are the same or different and are hydrogen, alkyl or aralkyl of 1–12 carbon atoms or a fluoride which is $KHF_2$, $NH_4HF_2$ or $KSO_2F$. The fluoride is activated by a complexing agent for the cation which is a cryptate, a cyclic or linear polyether or by means of a polar aprotic compound. The carbonate is split to give a reaction mixture containing an aldehyde and the fluoroformate which is removed from the reaction mixture.

17 Claims, No Drawings

PROCESS FOR THE PREPARATION OF FLUOROFORMATES

The present invention relates to a process for the preparation of fluoroformates of formula:

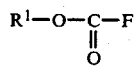

The fluoroformates are known compounds and have been in great demand particularly for the introduction of oxycarbonyl groups into a molecule, for instance in the synthesis of peptides.

Several processes for the preparation of fluoroformates have been proposed but they are not totally satisfactory. One of these processes consists of reacting a fluorocarbonyl halide with an alcohol or a phenol as described in the *J. Org. Chem.*, 21, p. 1319 (1956) according to the reaction hereinbelow:

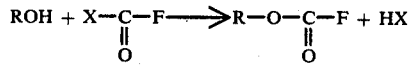

in which X is F, Cl, or Br.

This process, however, presents several drawbacks. The fluorocarbonyl halides are very difficult to prepare and consequently, not in everyday use. They are also difficult to handle and dangerous. The reaction temperature must be very low, in the neighborhood of $-70°$ C. and a complex cycle of temperature from $-70°$ C. up to $0°$ C. must be used, a fact which involves very high operating expenses. The fluoroformates thus obtained are impure due to the by-products formed, such as the carbonates or the unreacted starting materials. The yields are low, 50-55%. If one tries to improve the yields, it is necessary to carry out the reaction at high pressure, according to French Pat. No. 2,010,922, a fact which is not free from danger.

Another process for the preparation which is more feasible is carried out from the chloroformates by replacment of the chlorine with the fluorine atom by means of a fluoride. However, the reaction conditions, the high temperature or the presence of the catalysts do not always permit to obtain the desired fluoroformate, particularly when the chloroformate starting material is very unstable. For instance, the compound tertiary butyl chloroformate is decomposed rapidly and violently setting free isobutene, carbon dioxide and hydrochloric acid, as described in *J. Am. Chem. Soc.*, Vol. 79, page 4686 (1957). The formation of this compound in situ does not give better results, as reported in *J. Am. Chem. Soc.*, Vol. 88, page 852 (1966). When one uses, as the starting material, benzyl chloroformate, one obtains preponderantly benzyl chloride. The substitution of chlorine with a fluorine atom becomes even more difficult when the number of carbon atoms in primary or secondary chloroformates increases.

It is clear from the foregoing that it would be highly desirable to provide a general process for the preparation of a great number of fluoroformates suitable on a large scale, without substantial risk, at a low cost, with a high degree of purity and in particular the fluoroformates which have been more inaccessible.

The present invention resides in the preparation of fluoroformates of formula:

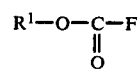

in which $R^1$ is an aliphatic, cycloaliphatic or polycyclic radical, which may be substituted or unsubstituted, saturated or unsaturated or an araliphatic radical which may be substituted or unsubstituted or an aromatic radical, by reacting a carbonate of formula:

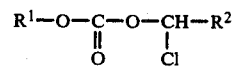

in which $R^1$ has the meaning indicated hereinabove and $R^2$ is hydrogen, alkyl of 1 to 12 carbon atoms or cycloalkyl of 5 to 12 carbon atoms, which may be saturated or unsaturated, unsubstituted or substituted by one or more halogen atoms, or $R^2$ is aryl, unsubstituted or substituted by one or more halogen atoms, with an alkali or alkaline earth, ammonium or quaternary ammonium fluoride. The quaternary ammonium fluoride has the formula:

$$FNR^3R^4R^5R^6$$

in which $R^3$, $R^4$, $R^5$ and $R^6$ are the same or different and are hydrogen or alkyl or aralkyl of 1 to 12 carbon atoms. The fluoride may also be $KHF_2$, $NH_4HF_2$ or $KSO_2F$. The fluoride is activated by a complexing agent of the cation which is a cryptate or a cyclic or linear polyether or by means of an aprotic polar compound. The reaction is carried out at a temperature between $20°$ and $120°$ C. The products, the fluoroformates or the aldehydes thus obtained or both substances are separated from the reaction medium as soon as formed. The reaction scheme may be represented by the following:

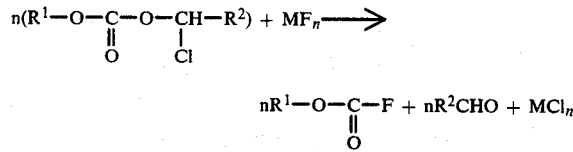

in which n is equal to 1 or 2. The reaction may be carried out in the absence or in the presence of a solvent which is inert to the reagents when one utilizes a complexing agent. The α-chloro carbonate starting materials are commercially available or are easily prepared by known methods, for instance by condensation of α-chlorinated chloroformates with hydroxylated compounds as described in *Chem. Rev.*, pages 654-687 (1964).

The radical $R^1$ may vary widely and may be an aliphatic, cycloaliphatic, polycyclic, araliphatic, or aromatic radical of 1-40 carbon atoms, preferably 1-24 carbon atoms. In general, when it is substituted, its substituents are selected among hydrocarbon radicals and halogen atoms. By way of example, the alkyl group may be: $CH_3$, $C_2H_5$, $nC_3H_7$, $i-C_3H_7$, allyl, $n-C_4H_9$, $t-C_4H_9$, $t-C_5H_{11}$, neopentyl, $n-C_8H_{17}$, octadecyl; The cycloalkyl and polycyclic groups may be: cyclohexyl, 1-adamantyl, cholesteryl; The aryl group may be:

phenyl or naphthyl; The aralkyl group may be: benzyl or halobenzyl. The compounds in which $R^1$ is tertiary aliphatic or tertiary cycloaliphatic radical are valuable, particularly the tertiary butyl radical.

For the purpose of simplification, the definition of $R^1$ hereinabove has been given considering that it is attached only to one carbonate function. It is certain, however, that within the scope of the invention, $R^1$ may be attached to one or more α-chlorinated carbonate functional groups and that the process of the invention permits to obtain polyfluoroformates, for instance alkyleneglycol bisfluoroformates starting from alkyleneglycol biscarbonates.

The radical $R^2$ is recovered in the aldehyde which is a by-product. There are many variations as to the nature of this radical. Most frequently, it is selected as a function of the ease of formation or elimination of the aldehyde or according to economical considerations.

By way of example, there may be mentioned for $R^2$: $CH_3$, $C_4H_9$, $CCl_3$, $CH_2=CH-$, cyclohexyl, phenyl, 1-chlorophenyl.

The radical $CCl_3$ is particularly valuable. Also, the vinyl radical is suitable. When $R^2$ is methyl, the carbonates are more accessible and the acetaldehyde which is formed is more easily removed from the reaction medium.

In accordance with the present invention, it has been found that surprisingly, the fluorides previously mentioned permit the cleavage of the α-chlorocarbonates and their transformation into fluoroformates. They are introduced most frequently in an amount between 1 and 5 equivalents, preferably between 1.2 and 3 equivalents with respect to the α-chloro carbonate. A great excess of the fluoride does not substantially improve the yield of the process. Potassium fluoride is in general the preferred reagent. The fluorides must necessarily be activated. Cryptates or crown ethers which form a complex with the cation perform this function very satisfactorily. They are described in the publication by Kappenstein, *Bull. Soc. Chem. of France* 1974, No. 1–2, pages 89–109, and in the publication by Lehn "Structure and Bonding", Vol. 16, pages 2–64, Springer Verlag (1974). The monoalkylethers of polyethyleneglycol of molecular weight between 500 and 10,000 may be equally used. There may be mentioned by way of example the monomethylether of average molecular weight equal to 5,000.

A very satisfactory complexing agent in particular in the case of potassium fluoride is a cryptate selected from the group of polyoxydiazamacrobicyclic compounds commercially sold by Merck under the trademark Kryptofix, such as for instance, hexaoxa-4,7,13,16,21,24 diaza-1,10 bicyclo [8,8,8] hexacosane or "Kryptofix 222" or a crown-ether such as 18-crown-6 or 1,4,7,10,13,16 hexaoxacylooctadecane. There is introduced in general, between 1 and 10% mole of this complexing agent with respect to the fluoride.

It is noted that the fluorides are equally activated when they are used in an aprotic polar medium. Anhydrous compound such as dimethylsulfoxide, hexamethylphosphorotriamide, N-methylpyrrolidone, sulfolane and preferably dimethylformamide are suitable.

In order to improve the experimental conditions, one may, when the fluoride is used in the form of a complex, use one or more anhydrous solvents which are inert with respect to the α-chloro carbonate. The dialkyl ether of alkyleneglycols or of a polyhydroxyalkyleneglycol, for instance the glymes, are very suitable. Other solvents such as dioxane and benzonitrile may equally be used.

The reactions are preferably carried out at a temperature between 30° and 70° C. When one prepares a fluoroformate which is unstable, obviously it is necessary to carry out the reaction at a temperature which is not too high. For instance, in the case of tertiary butyl fluoroformate, the temperature must be lower than 55° C.

In order to separate the fluoroformate and the aldehyde formed or one of these two substances from the reaction medium, every conventional procedure may be used. One method frequently used consists of evaporating continuously under reduced pressure, the two substances and separating them either by physical means such as fractional distillation or by chemical means. The aldehyde vapors which come from the reaction mixture may, for instance, be collected in an alcohol or a polyol in order to be converted into an acetal. When the fluoroformate is the more volatile compound, it is continuously removed from the reaction medium and may be purified by distillation. When the fluoroformate, on the other hand, remains in the reaction medium, one may carry out ordinary operations of washing, for instance with chloroform and ice water, and drying. The substance is then obtained by distillation under reduced pressure.

The process in accordance with this invention permits to prepare a great number of fluoroformates starting from accessible starting materials, in a high degree of purity and with excellent yield and in particular fluoroformates, the synthesis of which, up to the present time, has been difficult or impossible.

The process according to the present invention is particularly valuable for the preparation of tertiary butyl fluoroformate which has presented many problems according to known methods.

The majority of the fluoroformates obtained present sufficient stability, however, it may be desirable for some of the fluoroformates and, for instance in the case of tertiary butyl fluoroformate, to improve this property. It has been found that the addition to the fluoroformate after purification of a compound such as an alkali carbonate or an alkaline earth carbonate has a very favorable effect. For this reason, this compound is added to the fluoroformate in the ratio of 1–25%, in general, 5–10% by weight with respect to the latter. A very suitable substance is anhydrous sodium carbonate.

The fluoroformates have found many applications. They are useful for the preparation of alkyl fluorides, as described in French Pat. No. 1,549,815, Column 1, or aryl fluorides as described in *Chemical Abstracts*, Vol. 66, P. 18571. They are also very valuable in the synthesis of many organic compounds, for instance in the introduction of protecting groups of amine functional groups in a variety of polyfunctional compounds, particularly aminoacids in the chemistry of peptides, as described in U.S. Pat. No. 3,592,836; Houben Weyl, *Methoden der organischem Chemie*, Vol. 15, Part 1 Synthese von Peptiden, pp. 46–314, and as intermediates in the preparation of bactericides and fungicides as described in *Chemical Abstracts*, Vol. 76, P.24899.

The following examples illustrate the invention.

EXAMPLE 1

Preparation of Tertiary Butyl Fluoroformate (a) Preparation of tertiary butyl 1,2,2,2-tetrachloroethyl carbonate $$(CH_3)_3C-O-\underset{\underset{O}{\|}}{C}-O-\underset{\underset{Cl}{|}}{CH}-CCl_3$$

In a 4 l. reactor, there is introduced 1 l. of dichloromethane, 155 g (2.1 moles) of tertiary butyl alcohol and 493 g (2 moles) of 1,2,2,2-tetrachloroethyl chloroformate.

Under stirring and at a temperature between 0° and 5° C., there is added during the course of 1 hr., about 160 g (2.025 moles) of pyridine in 400 cc of dichloromethane. After stirring 4 hrs. at 5° C., the precipitate thus formed is filtered off and washed with 600 cc of dichloromethane. The solutions of dichloromethane are combined and washed with water up to neutrality, then dried over magnesium sulfate. After removal of the solvent under reduced pressure, the product is isolated in the form of white crystals. Yield: 518 grams (92%). The substance may be purified by distillation under reduced pressure.

b.p.: 96° C. under a pressure of 900 Pa.
m.p.: 70° C.
IR C=O : 1770 cm$^{-1}$
$^1$H NMR (CDCl$_3$, TMS, $\delta$ppm) : 1.5 (s, CH$_3$) 6.7 (s, CH).

(b) Preparation of Tertiary Butyl Fluoroformate

In a 2 l. reactor provided with a stirrer, thermometer, vertical reflux condenser, cooled with water at room temperature, connected to a tube dipped into a second reactor, there is introduced 100 g (1.7 moles) of potassium fluoride, 10 g (0.038 moles) of 18-crown-6. There is then added a solution of 300 cc (1.06 moles) of the carbonate prepared in part (a) in 300 cc of diethyleneglycol dimethylether.

In the second reactor provided with a reflux condenser and cooled by means of water, there is introduced 250 cc of diethyleneglycol dimethylether, 70 g of ethyleneglycol and 60 g of anhydrous magnesium sulfate. The mixture is kept at 30°-35° C. under stirring.

The reaction mixture from the first reaction vessel is kept at 50° under stirring. The two reactors are kept at a pressure of about 1.3 kPa. The reaction is allowed to proceed for 8 hrs. during which tertiary butyl fluoroformate and the chloral which are formed are continuously distilled off from the first reactor towards the second reactor where the aldehyde reacts with ethyleneglycol giving an acetal which is little volatile. Only the fluoroformate distills from the second reactor. The substance is condensed according to conventional methods, for instance in a trap maintained at −50° C. and connected with a vacuum pump.

After distillation under reduced pressure of the product thus isolated, one obtains 100 g (79% yield) of tertiary butyl fluoroformate as a liquid which distills at about 6°-8° C. at a pressure of 3.6 kPa (27 mm Hg).

IR C=O : 1830 cm$^{-1}$
$^1$H NMR (CDCl$_3$, TMS, $\delta$ppm) : 1.54 [d : $J_{H,F}$=1.47 Hz(CH$_3$)$_3$C]$^{19}$F (trifluoroacetic acid, $\delta$ppm) : 65.5 (s).
$N_D^{15}$ : 1.3615.
$d_4^{20}$ : 0.987.

EXAMPLE 2

Preparation of Tertiary Butyl Fluoroformate

In a reactor similar to the reactor used in Example 1 (b), there are introduced 389 g (1.37 moles) of tertiary butyl 1,2,2,2-tetrachloroethyl carbonate, 115 g (1.98 moles) of potassium fluoride in 700 cc of anhydrous dimethylformamide. The condenser is connected with a tube dipped into a second reactor which is provided with a distillation column, the latter being provided with Raschig rings and with a double jacket which permits to keep the temperature at 15° C. The column is connected with a trap kept at −70° C., the latter being connected with a vacuum pump. The assembly of the reactors and the trap are maintained at a pressure of about 2.7 kPa during the entire duration of the reaction.

In the second reactor, there are introduced initially 140 g (2.25 moles) of ethyleneglycol and 93 g (0.65 moles) of anhydrous sodium sulfate and the apparatus is kept at 30°-35° C. under stirring. The first reactor is kept at 50° C. for a period of 8 hrs. during which the fluoroformate which is formed condenses in the trap at −70° C. There is obtained 123.7 g (75% yield) of pure tertiary butyl fluoroformate, which exhibits the same properties as in Example 1 (b).

EXAMPLE 3

Preparation of Tertiary Butyl Fluoroformate

In a flask provided with a stirrer, a thermometer and a reflux condenser, are introduced 33.3 g (0.2 moles) of tertiary butyl chloromethyl carbonate, 15.1 g (0.26 moles) of potassium fluoride, 4.74 g (0.018 moles) of 18-crown-6 ether and 60cc of dioxane. The mixture is stirred for 24 hrs. at 50° C. By NMR analysis of the reaction medium, it is determined that the tertiary butyl fluoroformate is formed with about 40% yield.

EXAMPLE 4

Preparation of Phenyl Fluoroformate

A mixture of 11.6 g (0.058 mole) of freshly distilled 1-chloroethyl phenyl carbonate, 4.60 g (0.079 mole) of anhydrous KF (Aldrich), 0.80 g (0.003 mole) of 18-crown-6 ether (Aldrich) is prepared. The mixture is stirred and heated by means of an oil bath at 75° C. at a pressure of about 2.7 kPa. The reaction is allowed to proceed for 90 minutes during which the phenyl fluoroformate which is formed continuously evaporates and is removed by fractional distillation.

Yield: 70% (5.67 g).
b.p.: 60°-63° C. at 2.7 kPa (20 mm).
IR (CCl$_4$): 5.42 $\mu$(>C=O),6.29 $\mu$(m).
$^1$H NMR (CCl$_4$)$\delta$: 7.25 (broad s).

EXAMPLE 5

Preparation of Tertiary Butyl Fluoroformate

Freshly distilled tertiary butyl 1-chloroethyl carbonate, 5 g (0.03 mole) is added to 3 g (0.0516 mole) of anhydrous KF and 0.37 g (0.001 mole) of 18-crown-6 ether. The mixture is stirred and warmed at about 70° C. (oil bath) at a pressure of 4.9 kPa and the products which are formed are condensed in a trap at −80° C. A mixture of the aldehyde and the fluoroformate is collected during the course of 18 hrs. in the amount of 3.73 g. The mixture is heated at 50° C. in order to eliminate the acetaldehyde and then the residue is distilled under reduced pressure in order to isolate the pure fluoroformate. (b.p. : 45° C. at 27 kPa; 200 mm) The yield is 2.66 g (80%). Its IR and NMR properties are the same as in Example 1 (b).

EXAMPLE 6

Preparation of Ethyl Fluoroformate

A mixture of freshly distilled ethyl 1-chloroethyl carbonate in the amount of 6 g (0.04 mole), 10 g of anhydrous KF (0.17 mole), 2.4 g (0.01 mole) of 18-crown-6 ether in 17 cc of benzonitrile (Aldrich, dried over $CaCl_2$ and distilled under vacuum in the presence of $P_2O_5$) is placed in a reactor connected to a trap kept at −80° C. The mixture is stirred and warmed at 55° C. (oil bath) at a pressure of 4 kPa. After 13 hrs., there is collected in the trap 5 g of a mixture of acetaldehyde and ethyl fluoroformate. The yield of the latter by $^1H$ NMR analysis is 93%.

IR ($CCl_4$) : 5.46 μ, 8.01.

$^1H$ NMR ($CCl_4$,δppm) : 4.50 (q, 2H, J=7Hz), 1.44 (d of t, 3H, J=7 and 2Hz).

EXAMPLE 7

Preparation of n-octyl Fluoroformate

A mixture of 10.6 g (0.045 mole) of previously distilled octyl 1-chloroethyl carbonate, 4.5 g (0.08 mole) of dry KF and 0.6 g (0.002 mole) of 18-crown-6 ether is stirred and warmed at about 85° C. ( oil bath ) under a pressure of about 1.87 kPa. After 12 hrs., all the volatile acetaldehyde has evaporated. The mixture is cooled and distilled under reduced pressure. There is obtained 6.87 g of pure n-octyl fluoroformate (86%). b.p.: 74°-77° C. at 533 Pa (4 mmHg).

IR ($CCl_4$) : 5.46 μ.

$^1H$ NMR ($CCl_4$)δ4.20 (t, 2H, J=6Hz), 0.8-1.6 (m, 15 H).

EXAMPLE 8

Preparation of Tertiary Amyl Fluoroformate

A mixture of 10.4 g (0.054 mole) of 1-chloroethyl tertiary amyl carbonate, 4.5 g (0.077 mole) of dry KF and 0.67 g (0.0025 mole) of 18-crown-6 ether is stirred and warmed at about 70° C. (oil bath) under reduced pressure of 1.87 kPa. The volatile products are condensed in a trap kept at −80° C. as soon as they are formed. At the end of 34 hrs., there is obtained 8.18 g of a mixture of the aldehyde and tertiary amyl fluoroformate. By distillation under reduced pressure, there is obtained the pure fluoroformate, 5.99 g (83%) of b.p. 61°-65° C. at 17.3 kPa.

IR ($CCl_4$) : 5.46 μ(s).

$^1H$ NMR ($CDCl_3$, δ) : 1.85 (q, 2H, J=7Hz); 1.50 (d, J=1Hz, 6H); 0.93 (t, J=7Hz, 3H).

EXAMPLE 9

Preparation of 1-adamantyl Fluoroformate

A mixture of 9.93 g (0.038 mole) of 1-chloroethyl 1-adamantyl carbonate, 3.4 g (0.06 mole) of anhydrous KF and 0.43 (0.0016 mole) of 18-crown-6 ether is stirred and heated to about 120° C. (oil bath) under a pressure of 160 Pa. The acetaldehyde and the fluoroformate are distilled off continuously and the latter is prevented from solidifying in the condenser by means of a current of warm air. After 36 hrs., there is obtained 6.17 g of practically pure fluoroformate (about 1% of 18-crown 6 ether is detected by $^1H$ NMR analysis). Yield: 81%.

After distillation, the pure substance is obtained, 5.79 g (yield 76%) which solidifies in the receiving vessel.

b.p.: 71°-75° C. under a pressure of 160 Pa (1.2 mm). m.p.: 30°-32° C.

IR ($CCl_4$): 5.47 μ(s).

$^1H$ NMR ($CCl_4$) : δ2.18 (center of br s, 9H); 1.82 (center of br s, 6H).

EXAMPLE 10

Preparation of Benzyl Fluoroformate

A mixture of 8.01 g (0.037 mole) of 1-chloroethyl benzyl carbonate, 3.89 g (0.067 mole) of KF and 0.49 g (0.002 mole) of 18-crown-6 ether is heated under stirring to about 55° C. (oil bath) under a vacuum of 1.2 mm. The fluoroformate and the acetaldehyde which are formed are allowed to evaporate as soon as formed with the latter not being liquified in the condenser. After 4 hrs., the evaporation is completed by means of a hot air current (heat gun). There is obtained a mixture of the fluoroformate and the carbonate starting material which is distilled in order to isolate 3.45 g (60% yield) of pure benzyl fluoroformate.

b.p.: 44°-46° C. at 160 Pa.

IR ($CCl_4$): 5.45 μ.

$^1H$ NMR ($CCl_4$) δ7.42 (s,5H), 5.25 (s,2H).

EXAMPLES 11 and 12

The fluoroformates are prepared according to the following method: The carbonate, 1 equivalent, KF 1.6 equivalent, 18-crown-6 ether (0.06 equivalent) in tetraglyme are heated under stirring to a temperature of 50°-60° C. at a pressure of about 1.33 up to 2.7 kPa. The volatile material is evaporated continuously and collected in a trap at −70° C. The fluoroformate is then isolated by distillation.

Preparation of Isopropyl Fluoroformate:

This substance is prepared from isopropyl 1-chloro 1-(2-chlorophenyl)methyl carbonate of boiling point 100° C. at 27 Pa of formula hereinbelow:

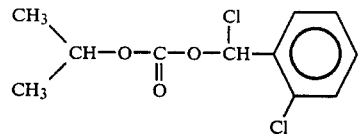

The reaction is allowed to proceed 13 hrs., after which isopropyl fluoroformate is obtained with 70% yield by $^1H$ NMR analysis.

IR C=O: 1830 $cm^{-1}$, broad band C—O—C at 1275 $cm^{-1}$.

$^1H$ NMR (δppm) : 1.4 (decoupled doublet, 6H); 4.95 (m, 1H).

Preparation of Cyclohexyl Fluoroformate:

The substance is prepared from cyclohexyl 1-chloropentyl carbonate of boiling point 90° C. at 20 Pa. A mixture of cyclohexyl fluoroformate and valeraldehyde is obtained. The yield of the fluoroformate is 20% according to $^1H$ NMR analysis.

b.p.: 55°-56° C. at 2.9 kPa.

IR C=O: 1830 $cm^{-1}$ broad band at 1275 $cm^{-1}$.

$^1H$ NMR ($CDCl_3$, δppm): 4.70 (m, 1H); 1.55 (m, 10H).

EXAMPLE 13

Preparation of n-octadecyl fluoroformate

A mixture of 4.65 g (0.012 moles) of 1-chloroethyl octadecyl carbonate, 1.39 g (0.0239 moles) of anhydrous KF and 0.25 g (0.95 mmole) of 18-crown-6 ether is heated under stirring to about 90° C. in an oil bath under a pressure of 666 Pa. After cooling, the mixture is diluted with 20 cc chloroform, then washed rapidly with ice water (3×15 cc) and dried over $Na_2SO_4$. On vacuum distillation, there is obtained 2.82 g of the pure fluoroformate (72% yield); b.p. 175°–180° C. at 3.33 kPa.

IR ($CCl_4$): 5.46 μ.

$^1$H NMR ($CCl_4$)δ: 4.25 (t, 2H, J=6Hz). 1.3 (broad s, 32H); 0.90 (t, 3H, J=6Hz).

EXAMPLE 14

Preparation of Neopentyl Fluoroformate (1) In this experiment 1-chloroethyl neopentyl carbonate is used as the starting material. A mixture of 5.50 g (0.028 mole) of 1-chloroethyl neopentyl carbonate, 2.5 g (0.043 mole) of anhydrous KF, 14 g of polyethyleneglycol monomethylether (average molecular weight 5000, Aldrich) and 15 cc of benzonitrile is heated under stirring at 60° C. ( oil bath ) under reduced pressure of 2.9 kPa. The products formed are condensed in a trap at −80° C. as soon as they are formed. There is obtained a mixture of 2.71 g of the aldehyde and the fluoroformate at the end of 3.5 days. By distillation, there is obtained 1.97 g of pure fluoroformate (52% yield).

b.p.: 55°–57° C. at 16 kPa.

IR ($CCl_4$): 5.46 μ.

$^1$H NMR ($CCl_4$)δ: 3.98 (s, 2H); 0.98 (s, 9H).

(2) In this experiment, neopentyl 1,2,2,2-tetrachloroethyl carbonate is used as the starting material. A mixture of 3.3 g (0.011 mole) of neopentyl 1,2,2,2-tetrachloroethyl carbonate, 1 g (0.017 mole) of anhydrous KF, 5 g (0.001 mole) of polyethyleneglycol monomethylether (average molecular weight 5000 Aldrich) and 10 cc of benzonitrile is heated under stirring at 65° C. (oil bath). The reaction is stopped at the end of 34 hours. By infrared and NMR analysis it is determined that the fluoroformate is obtained in a 76% yield.

EXAMPLE 15

Preparation of Cholesteryl Fluoroformate

A mixture of 1 g (0.002 mole) of cholesteryl 1-chloroethyl carbonate, 0.25 g (0.004 mole) of anhydrous KF, 0.05 g (0.2 mmole) of 18-crown-6 ether in 2 cc of benzonitrile is heated under stirring at about 40° C. (oil bath) at a pressure of 399 Pa. After 31 hours, the mixture is cooled to room temperature. It is then diluted with $CH_2Cl_2$, filtered and concentrated, the residue is recrystallized by addition of dry acetonitrile. There is obtained the fluoroformate, 0.72 g (82%).

m.p. : 114°–117° C.

IR ($CCl_4$): 5.48, 8.03 μ.

$^1$H NMR ($CCl_4$)δ: 5.2–5.5 (m); 4.2–4.6 (m); 0.7–2.6 (m).

EXAMPLE 16

Preparation of Tertiary Butyl Fluoroformate

A mixture of 9 g (0.047 mole) of tertiary butyl α-chloroallyl carbonate, 3.6 g (0.061 mole) of KF and 0.7 g (0.003 mole) of 18-crown-6 ether is heated at 70° C. at a pressure of 4.7–5.3 kPa. The fluoroformate and acrolein are collected in a trap kept at −80° C. The reaction is stopped after 10 hrs. By $^1$H NMR analysis, it is determined that the starting material, about 29%, is still present in the reaction vessel. The tertiary butyl fluoroformate is separated from acrolein by fractional distillation.

b.p.: 45°–46° at 26 kPa.

The yield is 3.2 g (55%).

What is claimed is:

1. A process for the preparation of fluoroformates of formula:

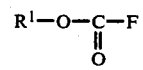

wherein $R^1$ is an unsubstituted saturated or unsaturated, aliphatic, cycloaliphatic or polycyclic radical of up to 24 carbon atoms, a saturated or unsaturated aliphatic, cycloaliphatic or polycyclic radical of up to 24 carbon atoms substituted by an hydrocarbon radical or by at least one halogen atom, araliphatic radical of up to 24 carbon atoms which is unsubstituted or substituted by an hydrocarbon radical or by at least one halogen atom, or an aromatic radical of up to 24 carbon atoms, which consists of reacting a carbonate of formula:

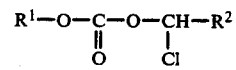

wherein $R^1$ has the same meaning as hereinabove and $R^2$ is hydrogen, alkyl of 1–12 carbon atoms, cycloalkyl of 5–12 carbon atoms, saturated or unsaturated, unsubstituted or substituted by one or more halogen atoms or $R^2$ is aryl, unsubstituted or substituted by one or more halogen atoms, with 1–5 equivalents of an alkali or alkaline earth fluoride, ammonium fluoride or a quaternary ammonium fluoride of formula $FNR^3R^4R^5R^6$, wherein $R^3$, $R^4$, $R^5$ and $R^6$ are the same or different and are hydrogen, alkyl or aralkyl of 1–12 carbon atoms or a fluoride which is a member selected from the group consisting of $KHF_2$, $NH_4HF_2$ or $KSO_2F$, said fluoride being activated by 1–10% by weight of a complexing agent for the cation in the fluoride which is a cryptate, a cyclic or linear polyether or being activated by a polar aprotic compound, at a temperature between 20° and 120° C., whereby said carbonate is split to give a reaction mixture containing an aldehyde of formula $R_2CHO$ and said fluoroformate, separating from the reaction mixture at least one of said fluoroformate and said aldehyde as soon as formed and recovering said fluoroformate.

2. The process according to claim 1 wherein said $R^1$ is a tertiary aliphatic, tertiary cycloaliphatic, polycycloaliphatic or benzyl.

3. The process according to claim 2 wherein said $R^1$ is tertiary butyl, tertiary amyl or 1-adamantyl.

4. The process according to claim 1 wherein $R^2$ is the radical $CCl_3$.

5. The process according to claim 1 wherein said polar aprotic compound is dimethylformamide, dimethylsulfoxide, hexamethylphosphorotriamide, N-methylpyrrolidone or sulfolane.

6. The process according to claim 1 wherein the fluoride is reacted in the proportion of 1.2–3 equivalents with respect to said carbonate.

7. The process according to claim 1 wherein said fluoride is potassium fluoride.

8. The process according to claim 7 wherein potassium fluoride is complexed with 18-crown-6 ether or "kryptofix 222".

9. The process according to claim 1, wherein said fluoride is complexed with a complexing agent for said cation and the reaction is carried out in the presence of at least one anhydrous solvent which is inert to said carbonate.

10. The process according to claim 9 wherein said solvent is an alkyleneglycol dialkylether or polyoxyalkylene glycol dialkyl ether, benzonitrile or dioxane.

11. The process according to claim 1 wherein said reaction temperature is 30°–70° C.

12. The process according to claim 1 wherein at least one of said aldehyde and said fluoroformate is separated from the reaction mixture by evaporation.

13. The mixture according to claim 1 wherein said fluoroformate is purified and then stabilized by addition of 1–25% by weight of an alkali or alkaline earth carbonate.

14. The process according to claim 13 wherein said alkali or alkaline earth carbonate is added in the amount of 5–10% by weight.

15. The process according to claim 1 wherein $R_2$ is $CH_3$, butyl, $CCl_3$, vinyl, cyclohexyl, phenyl, 1-chlorophenyl.

16. The process according to claim 1 wherein $R^1$ is alkyl of 1 to 18 carbon atoms, cyclohexyl, adamantyl, cholesteryl, phenyl, naphthyl, benzyl, halobenzyl.

17. The process according to claim 1, wherein $R^1$ is tertiary butyl and the reaction is carried out at a temperature lower than 55° C.

* * * * *